United States Patent
Kubo et al.

(10) Patent No.: US 10,365,264 B2
(45) Date of Patent: Jul. 30, 2019

(54) APPARATUS FOR MEASURING CONTRACTILE ABILITY OF MYOCARDIAL TISSUE

(71) Applicants: NIHON KOHDEN CORPORATION, Shinjuku-ku, Tokyo (JP); TOKYO WOMEN'S MEDICAL UNIVERSITY, Shinjuku-ku, Tokyo (JP)

(72) Inventors: Hirotsugu Kubo, Tokyo (JP); Tatsuya Shimizu, Tokyo (JP); Tetsutaro Kikuchi, Tokyo (JP)

(73) Assignees: NIHON KOHDEN CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 141 days.

(21) Appl. No.: 15/691,838

(22) Filed: Aug. 31, 2017

(65) Prior Publication Data
US 2018/0067098 A1    Mar. 8, 2018

(30) Foreign Application Priority Data
Sep. 2, 2016 (JP) .................. 2016-172126

(51) Int. Cl.
*G01N 33/483* (2006.01)
(52) U.S. Cl.
CPC ............... *G01N 33/4833* (2013.01)
(58) Field of Classification Search
CPC ................................. G01N 33/4833
See application file for complete search history.

(56) References Cited

U.S. PATENT DOCUMENTS

| | | | | |
|---|---|---|---|---|
| 6,482,619 B1* | 11/2002 | Rubinsky et al. | ..... | C12M 35/02 435/173.1 |
| 6,541,243 B1* | 4/2003 | Harris et al. | ........... | C12M 29/10 435/285.1 |
| 2003/0009112 A1* | 1/2003 | Hammerle et al. | .... | A61B 5/145 600/547 |
| 2010/0304423 A1* | 12/2010 | Asai et al. | ............ | B01L 3/5085 435/29 |
| 2011/0262958 A1* | 10/2011 | Yasuda et al. | ..... | G01N 33/5014 435/29 |

(Continued)

FOREIGN PATENT DOCUMENTS

JP    2013-518571 A    5/2013

OTHER PUBLICATIONS

Rambani, Komal, et al., "Culturing thick brain slices: An interstitial 3D microperfusion system for enhanced viability", Journal of Neuroscience Methods, Elsevier Science Publisher B.V., Jun. 15, 2009, vol. 180, pp. 243-254, Amsterdam, NL.

(Continued)

*Primary Examiner* — Gautam Prakash
(74) *Attorney, Agent, or Firm* — Pearne & Gordon LLP

(57) ABSTRACT

A measuring apparatus relates to a contractile ability of a spontaneously pulsating myocardial tissue. The measuring apparatus includes a measurement table and a pressure sensor. The measurement table includes a storage section having an opening and configured to hold liquid inside the storage section, and an attaching portion on which the myocardial tissue is attached around the opening. The pressure sensor is disposed inside the storage section.

6 Claims, 4 Drawing Sheets

(56) References Cited

U.S. PATENT DOCUMENTS

| | | |
|---|---|---|
| 2013/0217064 A1 | 8/2013 | Robitzki et al. |
| 2015/0322401 A1 | 11/2015 | Robitzki et al. |
| 2016/0030177 A1* | 2/2016 | Eschenhagen et al. ..................... A61B 5/1108 73/866.4 |
| 2017/0009207 A1* | 1/2017 | Shamir et al. ......... C12M 35/02 |

OTHER PUBLICATIONS

Extended European Search Report issued in Patent Application No. EP 17 18 8982 dated Dec. 20, 2017.
Article: Kubo, H., et al., "Creation of myocardial tubes using cardiomyocyte sheets and an in vitro cell sheet-wrapping device", Biomaterials Aug. 28, 2007,(24):35-08-16., Epub Apr. 18, 2007.

* cited by examiner

APPARATUS FOR MEASURING CONTRACTILE ABILITY OF MYOCARDIAL TISSUE

CROSS-REFERENCE TO RELATED APPLICATION

The present application claims priority from Japanese Patent Application No. 2016-172126 filed on Sep. 2, 2016, the entire content of which is incorporated herein by reference.

BACKGROUND

The presently disclosed subject matter relates to an apparatus for measuring contractile ability of a myocardial tissue.

A tissue structure having a stack of cell sheets and imitating a part of human heart is sometimes prepared for the purpose of application to a drug development study. Related art measuring apparatuses are used when evaluating contractile ability of such a tissue structure. For example, the measuring apparatus has a tissue structure having cardiomyocyte sheets wrapped around an outer circumference of a fibrin gel provided as a support member, and a measuring section configured to measure an action of the tissue structure as a pressure signal (see, e.g., Kubo H et al., "Creation of myocardial tubes using cardiomyocyte sheets and an in vitro cell sheet-wrapping device.", Biomaterials. 2007 August; 28(24):3508-16. Epub 2007 Apr. 18).

JP2003-518571A also discloses a related measuring apparatus.

In the related art measuring apparatuses, however, measured pressure signals sometimes contain a number of noise components that are difficult to remove even with a signal processing technique, in which case it is difficult to accurately evaluate the contractile ability of the prepared tissue structure.

SUMMARY

Illustrative aspects of the present invention provide a measuring apparatus which can quantitatively and accurately measure contractile ability of a myocardial tissue formed by cell sheets.

According to an illustrative aspect of the present invention, a measuring apparatus relates to a contractile ability of a spontaneously pulsating myocardial tissue. The measuring apparatus includes a measurement table and a pressure sensor. The measurement table includes a storage section having an opening and configured to hold liquid inside the storage section, and an attaching portion on which the myocardial tissue is attached around the opening. The pressure sensor is disposed inside the storage section.

Other aspects and advantages of the invention will be apparent from the following description, the drawings and the claims.

DETAILED DESCRIPTION

Hereinafter, a measuring apparatus according to an exemplary embodiment of the present invention will be described with reference to the drawings.

Figure 1:
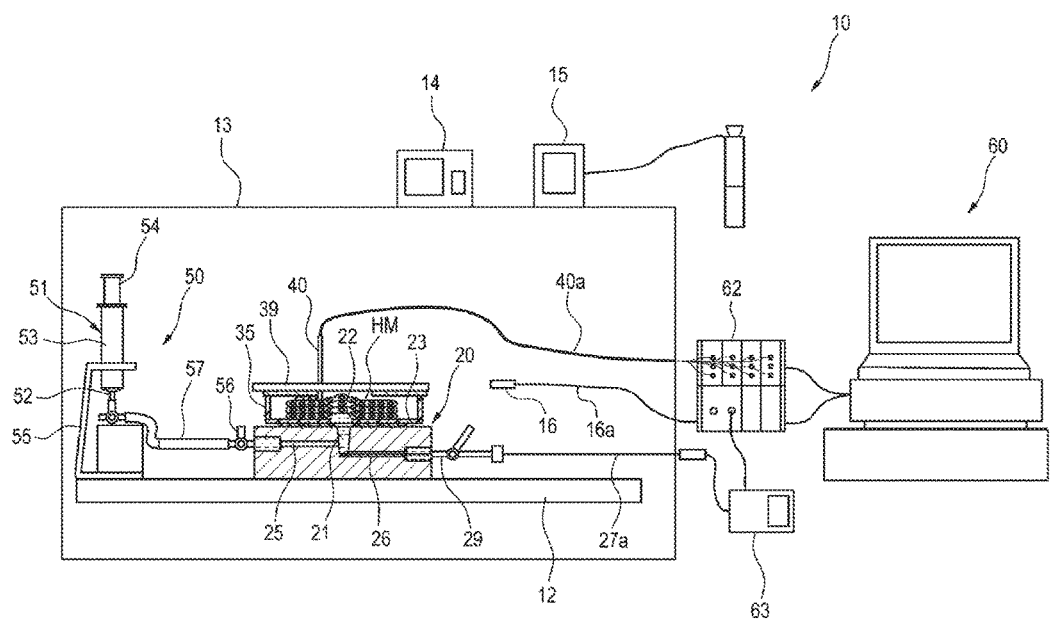
FIG. 1 is a configuration diagram illustrating a measuring apparatus according to an exemplary embodiment of the present invention.

FIG. 1 is a configuration diagram illustrating a measuring apparatus 10 according to an exemplary embodiment of the present invention. As shown in FIG. 1, the measuring apparatus 10 includes a measurement table 20, a reservoir 50, and a measurement device 60.

The measurement table 20 and the reservoir 50 are housed in a glove box 13 in a state in which they are disposed on an anti-vibration table 12 to suppresses vibration. The glove box 13 includes a temperature controller 14 and a $CO_2$ controller 15. A thermistor 16 is disposed in the glove box 13. Based on the temperature detected by the thermistor 16, the interior of the glove box 13 is kept at a constant temperature (for example, 37° C.) by the temperature controller 14. Moreover, the $CO_2$ concentration of the interior of the glove box 13 is kept at a constant value (for example, 5%) by the $CO_2$ controller 15.

Figure 2:
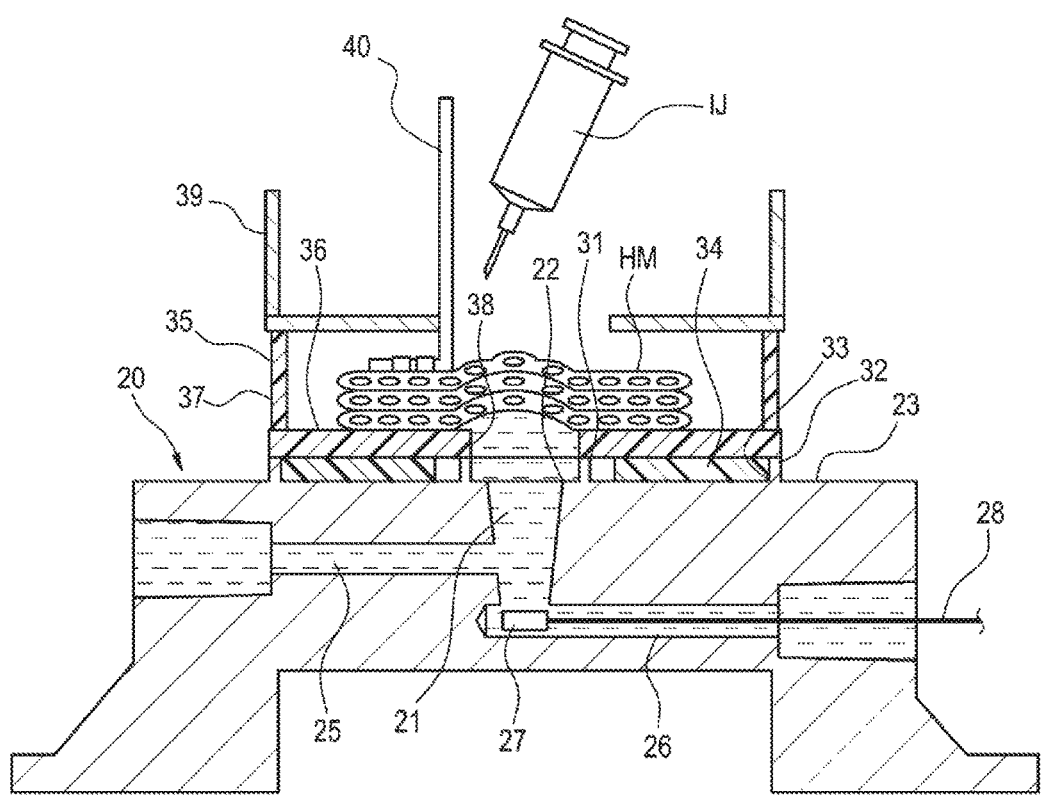
FIG. 2 is a sectional view of a measurement table of the measuring apparatus.

FIG. 2 is a sectional view of the measurement table 20 of the measuring apparatus 10. As shown in FIG. 2, the measurement table 20 has a storage section 21. The storage section 21 is a recess portion, and has an opening 22 at the upper surface of the measurement table 20. The storage section 21 is configured to hold cell culture solution inside the storage section 21. The opening 22 is disposed on the side of the measurement table 20 opposite to the gravitational direction. The measurement table 20 further includes an attaching portion 23 surrounding the opening 22.

In the measurement table 20, a culture solution injection path 25 and a sensor insertion path 26 are formed. The culture solution injection path 25 and the sensor insertion path 26 communicate with the storage section 21, and horizontally elongate from the storage section 21 in the opposite directions, respectively. The culture solution injection path 25 communicates with the storage section 21 at a vertically intermediate portion thereof, and opens on the side surface of the measurement table 20. The sensor insertion path 26 communicates with the storage section 21 at a lower end portion thereof, and opens on the side surface of the measurement table 20. A catheter 28 having a pressure sensor 27 is inserted into the sensor insertion path 26. The pressure sensor 27 is placed in the storage section 21. The pressure sensor 27 is configured to detect the pressure inside the storage section 21, and is disposed inside the storage section 21 at a position opposed to the opening 22. A sensor support tool 29 (see FIG. 1) is fitted to the sensor insertion path 26 into which the catheter 28 is inserted, so that the sensor insertion path 26 is sealed by the sensor support tool 29.

An annular inner protrusion 31, and an annular outer protrusion 32 having a larger diameter than the inner protrusion 31 are formed on the upper surface of the measurement table 20 which functions as the attaching portion 23. The inner protrusion 31 is formed so as to surround the opening 22. The outer protrusion 32 is formed concentrically with the inner protrusion 31. In the attaching portion 23 of the measurement table 20, therefore, an annular recess 33 is formed between the inner protrusion 31 and the outer protrusion 32. A water-tight sheet 34 which is formed into a sheet-like shape is placed in the annular recess 33. The water-tight sheet 34 is configured by, for example, forming a sheet made of silicone rubber or the like into an annular shape, and fitted into the annular recess 33.

A tray 35 is placed through the water-tight sheet 34 on the attaching portion 23 of the measurement table 20. The tray 35 is made of a transparent material such as glass or plastic, and has a disk-like bottom wall portion 36, and a peripheral wall portion 37 which erects from the peripheral edge of the bottom wall portion 36. A hole portion 38 is formed in the bottom wall portion 36 of the tray 35. The hole portion 38 communicates with the opening 22 of the storage section 21 of the measurement table 20. A bracket 39 is placed on the tray 35. The bracket 39 is fixed in a state in which the bracket is urged against the tray 35 by an elastic member such as rubber or a spring. Therefore, the tray 35 is attached to the attaching portion 23 of the measurement table 20 in a state in which the tray is pressed against the attaching portion by the bracket 39. Since the tray 35 is pressed against the attaching portion 23 of the measurement table 20, the water-tight sheet 34 is compressed to be closely contacted with the attaching portion 23 and the bottom wall portion 36 of the tray 35. As a result, the bottom wall portion 36 of the tray 35 is fixed to the attaching portion 23 of the measurement table 20 in a water-tight state.

A myocardial tissue HM (heart muscle tissue) is disposed in the tray 35. The myocardial tissue HM is configured by, for example, forming cardiomyocytes differentiated from human iPS cells into sheets, and stacking the cell sheets to form cardiomyocytes derived from human iPS cells into a stereoscopic (three-dimensional) tissue. The myocardial tissue HM is previously adhered and fixed to the bottom wall portion 36 of the tray 35. When the tray 35 to which the myocardial tissue HM is fixed is then attached to the measurement table 20, the myocardial tissue HM is attached to the attaching portion 23 of the measurement table 20 so as to close the opening 22 of the storage section 21 of the measurement table 20. As a result of the application, the storage section 21 forms a space which is isolated from the outside. The invention is applicable also to a myocardial tissue which is prepared by using cell sheets produced from a mouse or the like.

An electrode 40 configured by a conductive metal plate which is formed into an L-like shape is attached to the myocardial tissue HM attached to the attaching portion 23 of the measurement table 20. The electrode 40 detects the surface potential caused by pulsation of the myocardial tissue HM, and is attached the myocardial tissue HM provided on the attaching portion 23 at a periphery of a portion of myocardial tissue HM the covers the opening 22.

As shown in FIG. 1, the reservoir 50 has a pressurizer 51 (an example of the pressurizing section). In the exemplary embodiment, the pressurizer 51 has a tubular syringe 53 having an ejection port 52, and a plunger 54 which is inserted into the syringe 53. The pressurizer 51 is supported by a support table 55 in a state in which the ejection port 52 is directed toward the lower side. In the pressurizer 51, a supply pipe 57 having an on-off valve 56 is connected to the ejection port 52 of the syringe 53. The supply pipe 57 is connected to the culture solution injection path 25 of the measurement table 20. The cell culture solution is reserved in the pressurizer 51 of the reservoir 50. The cell culture solution is supplied to the storage section 21 from the pressurizer 51 through the supply pipe 57 and the culture solution injection path 25. By pushing the plunger 54 of the pressurizer 51 into the syringe 53, the cell culture solution supplied to the storage section 21 is pressurized.

Alternatively, the pressurizer 51 may be configured so as not to have the plunger 54. For example, the cell culture solution supplied to the storage section 21 can be pressurized by controlling the hydraulic head pressure of the cell culture solution inside the syringe 53 of the pressurizer 51.

Means for supplying the cell culture solution to the storage section 21 may not include a syringe, and it can be any means in so far as the cell culture solution can be supplied to the storage section 21. For example, a three-way stopcock may be used, so that the cell culture solution is supplied to the storage section 21 by opening and closing operations of the three-way stopcock.

The measurement device 60 measures the contractile ability of the myocardial tissue HM. The measurement device 60 includes an interface 62 and a controller 63. The interface 62 is connected to the main unit of the measurement device 60, and the controller 63 is connected to the main unit of the measurement device 60 through the interface 62. A wiring 40a extending from the electrode 40, and a wiring 16a extending from the thermistor 16 are connected to the interface 62. A wiring 27a extending from the pressure sensor 27 is connected to the controller 63.

An electric signal supplied from the electrode 40, a temperature detection signal supplied from the thermistor 16, and a pressure detection signal supplied from the pressure sensor 27 are transmitted to the main unit of the measurement device 60 through the interface 62. In the pressure sensor 27, a pressure measurement range and the like are controlled by the controller 63.

Next, a case where the contractile ability of the myocardial tissue HM is measured by the thus configured measuring apparatus 10 will be described.

Figure 3:
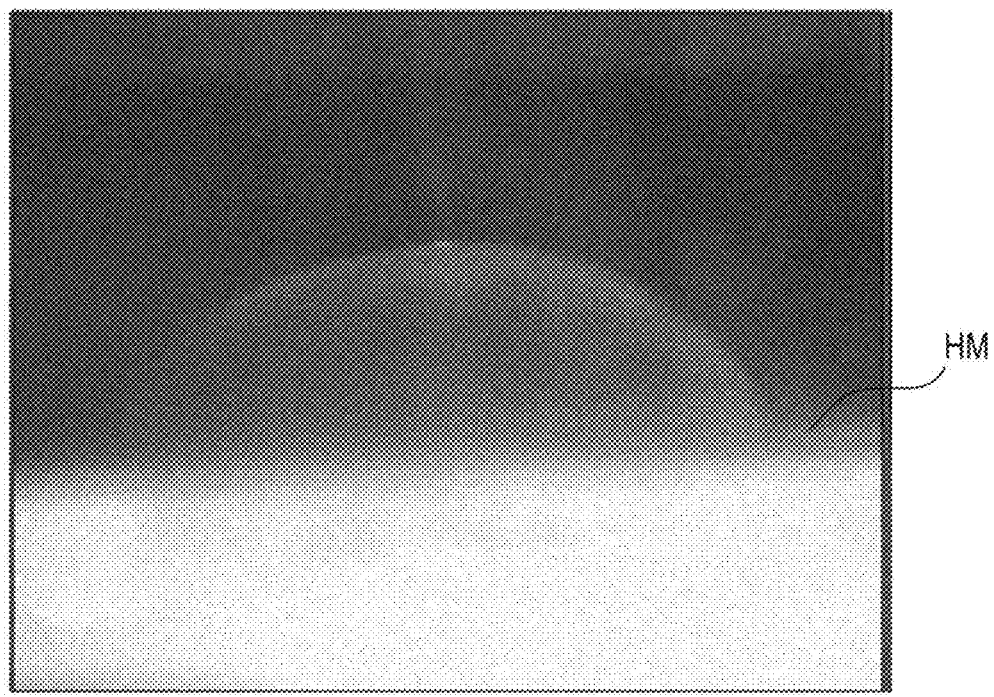
FIG. 3 is a side view of a myocardial tissue inflated into a dome shape by a pressure of cell culture solution.
Figure 4A:
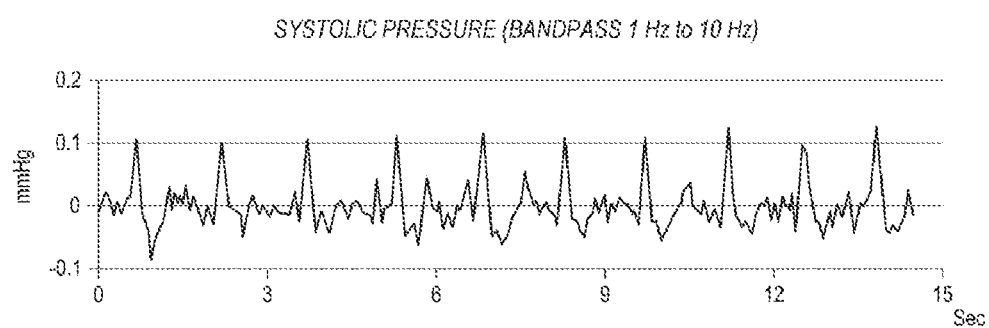
FIGS. 4A and 4B are graphs showing the pulsatile ability of the myocardial tissue measured by the measuring apparatus, FIG. 4A being a graph of the systolic pressure during the pulsation of the myocardial tissue, and FIG. 4B being a graph of the surface potential during the pulsation of the myocardial tissue.
Figure 4B:
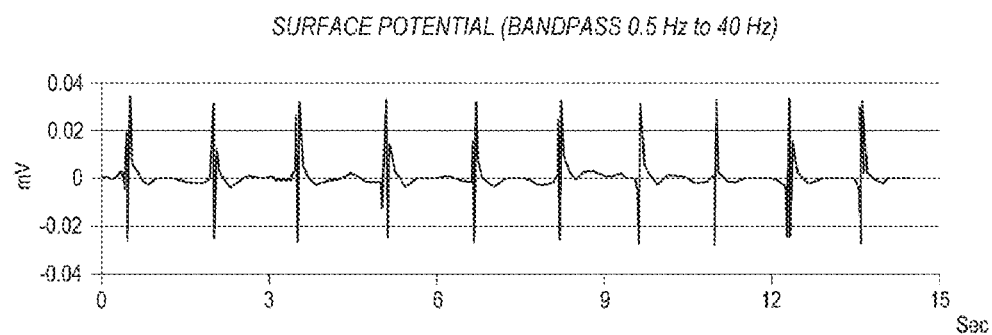

FIG. 3 is a side view of the myocardial tissue HM which is inflated into a dome shape by the pressure of the cell culture solution. FIGS. 4A and 4B are graphs showing the pulsatile ability of the myocardial tissue HM which was measured by the measuring apparatus 10, FIG. 4A is a graph of the systolic pressure during the pulsation of the myocardial tissue HM, and FIG. 4B is a graph of the surface potential during the pulsation of the myocardial tissue HM.

Firstly, the myocardial tissue HM is attached to the attaching portion 23 of the measurement table 20. Specifically, the water-tight sheet 34 is fitted into the annular recess 33 of the attaching portion 23 of the measurement table 20. Then, the tray 35 in which the myocardial tissue HM is previously adhered to the bottom wall portion 36 is placed on the attaching portion 23 through the water-tight sheet 34. The bracket 39 is placed on the tray 35, and then fixed to the attaching portion 23 in the state in which the bracket 39 is urged against the tray 35 by the elastic member. Thereafter, the electrode 40 is attached to the myocardial tissue HM at the periphery of the portion of the myocardial tissue HM that covers the opening 22. When the myocardial tissue HM is to be attached to the attaching portion 23, the cell culture solution is previously supplied from the reservoir 50 to the storage section 21 until the level of the solution reaches the vicinity of the opening 22 of the storage section 21, and, in this state, the on-off valve 56 is previously closed.

After the myocardial tissue HM is attached to the attaching portion 23 of the measurement table 20, the on-off valve 56 is opened, the plunger 54 of the pressurizer 51 of the reservoir 50 is plunged into the syringe 53, thereby pressurizing the cell culture solution. As shown in FIG. 3, therefore, the part of the myocardial tissue HM which covers the opening 22 of the storage section 21 is inflated into a dome shape by the pressure of the cell culture solution. At this time, the water-tight sheet 34 which is placed in the annular recess 33 between the inner and outer protrusions 31, 32 of the attaching portion 23 of the measurement table 20 is in close contact with the attaching portion 23 and the bottom wall portion 36 of the tray 35, and therefore the cell culture solution is prevented from leaking through a gap between the attaching portion 23 and the tray 35.

When the myocardial tissue HM is provided on the attaching portion 23 so as to close the opening 22 of the storage section 21 as described above, the myocardial tissue HM is in the state in which the myocardial tissue is in contact with the cell culture solution inside the storage section 21, and continues the spontaneous pulsation.

When the myocardial tissue HM spontaneously pulsates, the pressure in the storage section 21 varies, and the pressure variation is detected by the pressure sensor 27. As shown in FIG. 4A, therefore, the measurement device 60 acquires temporally sequentially the muscle contraction ability occurring during the pulsation of the myocardial tissue HM, as the systolic pressure based on the detection signal supplied from the pressure sensor 27.

When the myocardial tissue HM spontaneously pulsates, moreover, a minute electric potential is generated in the myocardial tissue HM during the spontaneous pulsation, and is detected by the electrode 40. As shown in FIG. 4B, therefore, the measurement device 60 acquires temporally sequentially the surface potential which is generated during the pulsation of the myocardial tissue HM.

In this state, a screening evaluation of test compounds such as medicines is performed for the drug development study. Specifically, a test compound which is to be evaluated is dripped onto the myocardial tissue HM by an injector IJ (see FIG. 2) or the like, and changes of the systolic pressure and surface potential of the myocardial tissue HM are observed. Then, the medicinal effect, toxicity, and the like of the test compound with respect to the myocardial tissue HM are evaluated based on the changes of the systolic pressure and surface potential of the myocardial tissue HM.

At this time, the motion of the myocardial tissue HM can be observed visually and easily through the peripheral wall portion 37 of the tray 35 because the tray 35 to which the myocardial tissue HM is attached is made of the transparent material.

As a test for evaluating the safety and effectiveness of a developed medicine, known are an in vitro test and an in vivo test. In an in vitro test, a single-cell cultivation system is used, and, in an in vivo test, an evaluation system for experimental animals centered on rodents is used.

It is said that the success rate in drug development is about 1/6000. Because of many failures, the cost of research and development of a medicine tends to be increased. For example, development of one kind of medicine requires an investment of several ten billion yen. Major causes of failures in development are the difference between an evaluation screening system for stand-alone cells and an actual living tissue of a human, that between an animal experiment and a human clinical trial, and the like. In the field of drug development, therefore, it is requested to eliminate these differences, improve the success rate in drug development, and reduce the cost of research and development.

In the measuring apparatus 10 of the exemplary embodiment, by using the cell sheet engineering, the three-dimensional myocardial tissue HM derived from human iPS cells is prepared, and the systolic pressure and the surface potential are measured while causing the test compound to act on the myocardial tissue HM, whereby an evaluation of the medicinal effect and a toxicity test are performed with respect to the myocardial tissue HM.

In the measuring apparatus 10 of the exemplary embodiment, as compared with the conventional technique in which a tissue is prepared by embedding cells in a scaffold material, as described above, the difference between reactions of stand-alone cells and a living tissue can be absorbed by using a highly integrated scaffold-less tissue which is more analogous to the living body, the difference due to the difference in species between an animal and the human can be eliminated, and the number of animal experiments can be reduced.

In the measuring apparatus 10 of the exemplary embodiment, moreover, the myocardial tissue HM derived from human iPS cells which have functional and gene expressions that are more analogous to those of the living body is used, and therefore it is possible to expect a test result to which a reaction in the living body is directly reflected, also as compared with the evaluation which uses stand-alone cells, and in which the stand-alone cells are electrophysiologically analyzed by the patch-clamp method or the like, and influences on ion channels that govern the cardiac systole and the action potential formation are investigated to test the medicinal effect and the toxicity.

In the measuring apparatus 10 of the exemplary embodiment, without using a soft material such as a pharmed tube, furthermore, the whole piping system for the cell culture solution is configured by rigid materials, and both isometric and isobaric contractions of the myocardial tissue HM can be measured by controlling the ON/OFF action of the on-off valve 56 and the pressurization by the pressurizer 51.

According to the measuring apparatus 10 of the exemplary embodiment, in the case where the myocardial tissue HM spontaneously pulsates in the state in which the myocardial tissue is in contact with the cell culture solution in the storage section 21, as described above, the pressure of the cell culture solution in the storage section 21 is affected and changed by the spontaneous pulsation. The pressure change due to the spontaneous pulsation can be accurately measured as a pressure signal by the pressure sensor 27 disposed inside the storage section 21. With respect to the myocardial tissue HM which is prepared by using cardiomyocyte sheets, therefore, the contractile ability of the tissue can be measured quantitatively and accurately.

The myocardial tissue HM can absorb nutrients from the cell culture solution, and pulsate continuously and spontaneously. Therefore, the contractile ability of the myocardial tissue HM can continue to be measured quantitatively, continuously, and accurately.

Moreover, the myocardial tissue HM provided on the attaching portion 23 of the measurement table 20 can spontaneously pulsate while being in contact with the cell culture solution, in the state in which the portion covering the opening 22 of the storage section 21 is inflated due to the pressurization by the pressurizer 51 of the reservoir 50 that is filled with the cell culture solution, and the tension is high (the myocardial tissue is stretched). When a myocardial tissue formed by the myocardial tissue HM is made three-dimensional as described above, the contractile ability can be measured more accurately as the pressure signal in a quantitative manner.

Since the pressure sensor 27 is disposed in the storage section 21 at the position opposed to the opening 22, the pressure sensor 27 can easily detect a pressure change of the cell culture solution inside the storage section 21 caused by spontaneous pulsation of the myocardial tissue HM. Therefore, the pressure signal in which the contractile ability is reflected can be measured further accurately.

Moreover, the surface potential which is generated in accordance with spontaneous pulsation of the myocardial tissue HM can be detected and measured simultaneously with the pressure signal by the electrode 40 attached to the myocardial tissue HM. Therefore, multiple parameters such as pressure and voltage signals corresponding to an electrocardiogram obtained from a living body can be measured in parallel on a common time axis, with the result that the prepared myocardial tissue HM can be easily evaluated, and also the influence of a reagent, and the like can be easily evaluated.

Furthermore, the electrode 40 is attached to the myocardial tissue HM provided on the attaching portion 23 at the periphery of the portion of the myocardial tissue HM that covers the opening 22. Therefore, it is possible to reduce influences of noises due to, for example, positional misalignment of the electrode 40 caused by spontaneous pulsation of the myocardial tissue HM.

Furthermore, the opening 22 of the storage section 21 of the measurement table 20 is provided on the side opposite to the gravitational direction. Therefore, the cell culture solution can be easily hold inside the storage section 21, and the pressure change can be detected further easily by the pressure sensor 27.

While the present invention has been described with reference to a certain exemplary embodiment thereof, the scope of the present invention is not limited to the exemplary embodiment described above, and it will be understood by those skilled in the art that various changes and modifications may be made therein without departing from the scope of the present invention as defined by the appended claims.

What is claimed is:

1. A measuring apparatus relating to a contractile ability of a spontaneously pulsating myocardial tissue, the measuring apparatus comprising:
   a measurement table;
   wherein the measurement table comprises:
      a tray for containing the myocardial tissue, wherein the tray comprising a bottom wall portion, and wherein the bottom wall portion comprises a hole portion;
      a storage section having an opening and configured to hold liquid inside the storage section, the opening in fluidic connection with the hole portion;
      an attaching portion on which the myocardial tissue is attached around the opening;
   a cell culture solution injection path disposed below and in fluidic connection with the opening;
   a pressurizing device in fluidic connection with the cell culture solution injection path and configured to pressurize the liquid supplied in the storage section through the cell culture solution injection path; and
   a pressure sensor, wherein the pressure sensor is disposed inside the storage section in a position opposed to the opening.

2. The measuring apparatus according to claim 1, wherein the storage section is configured to hold cell culture solution as the liquid inside the storage section.

3. The measuring apparatus according to claim 1, wherein the pressurizing device comprises a reservoir configured to be filled with the liquid.

4. The measuring apparatus according to claim 1, wherein the opening is provided to be opened in a direction opposite to a gravitational direction.

5. The measuring apparatus according to claim 1, wherein the measuring apparatus further comprises an electrode arranged to be attached to the myocardial tissue and configured to detect electric potential of the myocardial tissue.

6. The measuring apparatus according to claim 5, wherein the electrode is arranged to be attached to the myocardial tissue provided on the attaching portion at a periphery of a portion of the myocardial tissue that covers the opening.

* * * * *